United States Patent [19]

Kent et al.

[11] Patent Number: 4,827,070

[45] Date of Patent: May 2, 1989

[54] PROCESS FOR THE PRODUCTION OF ISOBUTYLBENZENE FROM AN ISOBUTENYLCYCLOHEXENE

[75] Inventors: Alexander G. Kent, North Humberside; Derek K. MacAlpine, Haywards Heath, both of United Kingdom

[73] Assignee: BP Chemicals Limited, London, England

[21] Appl. No.: 164,835

[22] Filed: Mar. 7, 1988

[30] Foreign Application Priority Data

Mar. 10, 1987 [GB] United Kingdom ............... 8705565

[51] Int. Cl.$^4$ .................. C07C 5/333; C07C 5/367
[52] U.S. Cl. ................... 585/430; 585/433; 585/434; 585/435; 585/443
[58] Field of Search ............ 585/430, 434, 433, 435, 585/443

[56] References Cited

U.S. PATENT DOCUMENTS

| | | | |
|---|---|---|---|
| 3,449,455 | 6/1969 | Napolitano et al. | 260/668 |
| 3,855,327 | 12/1974 | Billings | 585/433 |
| 4,029,715 | 6/1977 | Rieve et al. | 585/433 |
| 4,300,010 | 11/1981 | Cihonski | 585/434 |
| 4,308,413 | 12/1987 | de Graaf et al. | 585/430 |
| 4,429,175 | 1/1984 | Cihonski | 585/434 |
| 4,665,252 | 5/1987 | Hoelderich et al. | 585/431 |
| 4,720,603 | 1/1988 | Martin et al. | 585/431 |

FOREIGN PATENT DOCUMENTS

| | | | |
|---|---|---|---|
| 0022297 | 1/1981 | European Pat. Off. | 585/434 |
| A 10196165 | of 1986 | European Pat. Off. | |
| 2256449 | 5/1974 | Fed. Rep. of Germany | 585/433 |

OTHER PUBLICATIONS

"Preparation of Isobutylbenzene" Patent Abstracts of Japan, The Patent Office Japanese Gov., vol. 2, No. 118(C-111)[966] Jul. 2, 1982, Kokai No. 57-46927(A).
"Preparation of Alkenyl Substd..." Patent Abstracts of Japan, The Patent Office of Japan, vol. 2, No. 85, Jul. 12, 1978, Kokai No. 53-44525.

Primary Examiner—Patrick P. Garvin
Assistant Examiner—E. D. Irzinski
Attorney, Agent, or Firm—Nixon & Vanderhye

[57] ABSTRACT

An isobutylbenzene (IBB) is produced from an isobutenylcyclohexane (IBCH) by contacting at elevated temperature the IBCH in the presence of a molecular oxygen-containing gas with a catalyst comprising a supported transition metal in the form of the elemental metal and/or a compound thereof, for example palladium supported on alumina.

9 Claims, No Drawings

PROCESS FOR THE PRODUCTION OF ISOBUTYLBENZENE FROM AN ISOBUTENYLCYCLOHEXENE

The present invention relates to a process for the production of an isobutylbenzene (IBB) from an isobutenylcyclohexene (IBCH).

Isobutylbenzene itself is a high value speciality chemical used, for example, as an intermediate in the preparation of analgesics. Conventionally, isobutylbenzene is produced industrially by the side chain alkylation of toluene with propylene using an alkali metal catalyst. The alkali metal catalyst can be a liquid potassium, a liquid potassium/sodium eutectic or an alkali metal supported on a diatomaceous earth as disclosed in for example U.S. Pat. No. 3,449,455. The above process has a number of disadvantages when operated commercially since the alkali metal catalyst is (a) expensive, (b) inflammable and difficult to handle, and (c) short lived owing to gum formation. In addition there is formed, as a by-product, substantial quantities of n-butylbenzene which has to be separated subsequently from the isobutybenzene.

In our European application publication No. 0196165 we describe a two stage process which avoids the problems associated with the alkylation route and allows isobutylbenzene to be produced selectively.

The process disclosed therein is a process for the production of an isobutylbenzene from a vinylcyclohexene and an isoolefin which process comprises:
(1) in a first stage contacting the vinylcyclohexene and isoolefin with a dismutation catalyst under dismutation conditions to produce an isobutenylcyclohexene and another olefin,
(2) in a second stage contacting the isobutenylcyclohexene produced in the first stage with a dehydroisomerisation catalyst at elevated temperature to produce the isobutylbenzene.

By dehydroisomerisation we mean a combination of isomerisation and dehydrogenation/aromatisation.

In the second stage of this process IBCH is dehydroisomerised to IBB, which reaction may in addition to IBB produce by-products having a boiling point sufficiently close to that of isobutylbenzene as to make distillative separation difficult. In the specific case of isobutylbenzene itself the following potential by-products may be formed:

| Molecular Weight | Product |
| --- | --- |
| 132 | isobutenylbenzene |
| 132 | n-butenylbenzene |
| 134 | n-butylbenzene |
| 138 | isobutylcyclohexene isomers |
| 138 | isobutenylcyclohexane isomers |
| 138 | n-butylcyclohexene isomers |
| 138 | n-butenylcyclohexane isomers |
| 138 | methylbutylcyclopentene isomers |
| 140 | isobutylcyclohexane |
| 140 | methylbutylcyclopentane |

For the overall economics of the process in general and for drug production usage in particular, the highest selectivity and conversion to isobutylbenzene are very desirable. For example, isobutylbenzene for use as a feedstock for the synthesis of the drug IBUPROFEN has a typical specification of greater than 99.5% purity. It is therefore an important objective to minimise the production of any or all of the potential impurities identified hereinbefore. Low selectivity to isobutylbenzene will incur high separation costs.

We have found that this objective can be at least in part achieved if the dehydroisomerisation reaction is carried out in the presence of molecular oxygen.

Accordingly, the present invention provides a process for the production of an isobutylbenzene (IBB) from an isobutenylcyclohexene (IBCH) which process comprises contacting at elevated temperature an IBCH in the presence of a molecular oxygen-containing gas with a catalyst comprising a supported transition metal in the form of the elemental metal and/or a compound thereof.

The cyclohexene ring of the IBCH may be substituted with, for example alkyl or aryl groups, in which case the IBB resulting from the use thereof will be correspondingly substituted. It is preferred to use unsubstituted IBCH. The IBCH may be obtained from any source, but is preferably obtained by the dismutation reaction forming the first stage of our copending European application publication No. 0196165.

The molecular oxygen-containing gas may be oxygen itself, or may be oxygen diluted with one or more inert gases. A preferred gas is oxygen diluted with nitrogen. Air may also be used if desired. The molar ratio of oxygen to IBCH is an important parameter, which to some extent is related to the temperature and pressure of operation. At high oxygen to IBCH ratios it is our experience that isobutenylbenzene becomes a significant by-product whereas at low oxygen to IBCH ratios isobutylcyclohexane becomes a significant by-product. It is therefore desirable to operate at intermediate oxygen:IBCH ratios. It is of course desirable at all times to operate outside the oxygen:IBCH explosive limits. It is believed that some or all of the oxygen present is consumed to produce water (by reaction with hydrogen) and small amounts of carbon monoxide and carbon dioxide.

Whilst the reaction may be operated in the liquid phase, it is very much preferred to operate in the gaseous phase. Because of the very exothermic nature of the reaction, it is preferred to employ a gas phase reactor of such design that reaction exotherms are minimised or avoided, because such exotherms may lead to loss in selectivity to IBB.

As regards the catalyst, the term 'transition metal' for the purpose of the present specification is a metal capable of existing in the form of more than one valency and having an incompleted shell in at least one of its oxidation states. Transition metals include metals of Groups IB, IIB, IIIA, IVA, VIB, VIIB and VIII of the Periodic Table of the Elements as published by Sargent-Welch Scientific Company, Skokie, Ill., USA. Examples of suitable transition metals include cobalt, nickel, ruthenium, rhodium, palladium, iridium, platinum and mixtures of two or more thereof. A preferred metal is palladium.

The support may suitably be a refractory oxide, for example silica, alumina, silica-alumina, magnesia, titania, ceria, or the like. Carbon may also be used as a support, but metal oxides are preferred. A preferred support is alumina.

The catalysts for use in the process of the invention may be prepared by any of the techniques conventionally employed for the production of supported catalysts, such as by impregnation, coprecipitation or by ion-exchange. Suitably the catalyst may be prepared by an impregnation technique, for example the excess solution technique or the incipient wetness technique. The support may be impregnated with a solution of a soluble transition metal compound.

The catalyst may suitably comprise from 0.01 to 20%, preferably from 0.1 to 10% w/w of the transition metal, based on the weight of the support.

A preferred catalyst is palladium supported on alumina.

The process may be operated over a wide range of temperature and pressure conditions. In the preferred mode of operating the process, i.e. in the gas phase, ambient pressure and a temperature greater than the boiling point of IBCH may suitably be employed. In the case where IBCH is isobutenylcyclohexene, generally temperatures greater than 180° C. may be employed with temperatures in the range from 200° to 350° C. being preferred. Generally, at lower temperatures the production of by-product isobutylcyclohexane is favoured, whereas at higher temperatures isobutylcyclohexene and isobutenylbenzene production dominate. In consequence the use of an intermediate temperature in the range from 200° to 350° C. is preferred with respect to minimising by-product formation. Although the pressure may suitably be atmospheric, both subatmospheric and superatmospheric pressures may also be employed.

The process may be operated batchwise or continuously. It is preferably operated by cofeeding gaseous IBCH and oxygen diluted with nitrogen continuously over the supported catalyst, which may be in the form of, for example, a fixed bed, a fluid bed or a moving bed. The liquid hourly space velocity (LHSV), defined as the volume of liquid phase reactants (prior to vapourisation) per volume of catalyst per hour, may also be varied over a wide range. Typically LHSVs from about 0.1 to 150 are suitable. A particularly suitable LHSV is about 10.

The process of the present invention will now be further illustrated by reference to the following Examples.

EXAMPLES

Catalyst Preparation

Pd nitrate/gamma-alumina (2% w/w Pd)

Palladium (II) nitrate trihydrate (0.270 g) was dissolved in water (21.0 ml) and added to gamma-alumina (5.0 g, from calcination of Catapal SB boehmite alumina in air at 580° C.) with stirring. Water was slowly removed in vacuo keeping the catalyst temperature about 55° C. and the catalyst was then dried further at 100° C. for 12 hours.

COMPARISON TEST 1

Batch Liquid Phase Dehydroisomerisation of Isobutenylcyclohexene

A commercial 5% palladium/alumina (0.1 g) and isobutenylcyclohexene (5.0 ml) were placed in a glass flask under nitrogen and boiled under reflux with stirring. Analysis (by gas chromatography) of the mixture after one hour showed it contained 66.2% w/w isobutylbenzene and 30.7% w/w isobutylcyclohexane. This is not an example according to the present invention because oxygen was not used. It is included only for the purpose of comparison.

COMPARISON TEST 2

Gas Phase Dehydroisomerisation of Isobutenylcyclohexene

Isobutenylcyclohexene vapour was passed over a 2% palladium/alumina (1.0 g) catalyst packed in a glass reactor at a LHSV of 1 and a reaction temperature of 350° C. Analysis by gas chromatography of the condensed liquid product collected during the 1.3 hours following start-up showed it contained 93.5% isobutylbenzene and 0.1% isobutylcyclohexane.

This is not an example according to the present invention because oxygen was absent. It is included only for the purpose of demonstrating that gas phase operation is preferred over liquid phase operation, cf Comparison Test 1.

EXAMPLE 1

Palladium (II) nitrite on alumina (1.0 g, prepared as above) was packed into a glass tube reactor and purged with nitrogen (5.0 liters/hour) for 0.25 hours. The tempereature was then raised to 300° C. at 12° C./min. The nitrogen flow was then stopped and isobutenylcyclohexene in vapour form and 10% oxygen in nitrogen cofeed (average flow rate=0.48 liters/hour) were then passed over the catalyst at an LHSV of 1. The reaction products were condensed and liquid samples were obtained and analysed by gas chromatography. Table 1 shows the results obtained.

COMPARISON TEST 3

The experimental procedure was similar to Example 1 except that a nitrogen cofeed (average flow rate=0.55 liters/hour) was employed once the catalyst had been brought to 300° C. Table 2 shows the results obtained.

This is not an example according to the present invention because oxygen was not employed. It is included only for the purpose of comparison.

Comparistion of Example 1 with Comparison Test 3 shows that isobutylcyclohexane production does not increase with time on stream when an oxygen cofeed is employed.

EXAMPLE 2

The Effect of Reaction Temperature

Palladium (II) nitrate on alumina (1.0 g, prepared as above) was packed into a glass tube reactor and purged with nitrogen (5.0 liters/hour) for 0.25 hours. The temperature was then raised to 225° C. at 12° C./min. Isobutenylcyclohexene in vapour form and 10% oxygen in nitrogen were then passed over the catalyst at an LHSV of 1. The reaction products were condensed and liquid samples were obtained and analysed by gas chromatography. The reaction temperature was increased in steps of 25° C. over the course of the experiment. The results obtained are shown in Table 3.

These experiments show the effect of reaction temperature on selectivty to isobutylbenzene, isobutylcyclohexane, isobutylcyclohexene and isobutenylbenzene.

EXAMPLE 3

Oxidative Dehydroisomerisation at LHSV=10

The experimental procedure was similar to that of Comparison Test 3 except that 0.1 g of catalyst was employed to give a LHSV of 10 and 10% oxygen in nitrogen cofeed was used. Table 4 shows the results obtained.

COMPARISON TEST 4

Dehydroisomerisation at LHSV=10

Palladium nitrate/alumina (0.1 g, 2% Pd) was packed into a glass tube reactor and purged with nitrogen (5.0 liters/hour) for 0.95 hours. It was then treated with hydrogen (5.0 liters/hour) for 0.25 hours and heated to 350° C. at 12° C./min. The hydrogen was then shut off and isobutenylcyclohexene in vapour form passed over the catalyst at an LHSV of about 10. The reaction products were condensed and liquid samples were obtained and analysed by gas chromatography. Results obtained are shown in Table 5.

This is not an example according to the present invention because oxygen was not present. It is included only for the purpose of comparison. Comparing the results reported in Table 4 with those in Table 5, it is readily apparent that co-feeding oxygen has a beneficial effect on conversions and selectivities.

TABLE 1

Lifetime Study of the Dehydroisomerisation of Isobutenylcyclohexene Over a Palladium Nitrate on Alumina Catalyst with 10% Oxygen in Nitrogen Cofeed at 300° C.
This experiment shows that isobutylcyclohexane production does not increase with time on stream when an oxygen/nitrogen cofeed is employed.

Liquid Products (% w/w)

| Time on Stream (hours) | isobutyl-benzene | isobutyl-cyclo-hexane | isobutyl-cyclo-hexene | iso-butenyl-benzene | Selectivity to isobutyl-benzene |
|---|---|---|---|---|---|
| 2.0 | 96.39 | 0.28 | 0.05 | 0.21 | 96.4 |
| 5.0 | 96.88 | 0.25 | 0.08 | 0.19 | 96.9 |
| 8.0 | 96.47 | 0.20 | N/D | 0.20 | 96.5 |
| 11.0 | 96.83 | 0.18 | 0.09 | 0.22 | 96.8 |
| 14.0 | 96.87 | 0.16 | 0.09 | 0.22 | 96.9 |
| 17.0 | 96.97 | 0.16 | 0.08 | 0.23 | 96.9 |
| 20.0 | 96.71 | 0.16 | 0.09 | 0.23 | 96.7 |
| 23.0 | 97.03 | 0.15 | N/D | 0.22 | 97.0 |
| 26.0 | 96.61 | 0.15 | 0.08 | 0.22 | 96.6 |
| 29.0 | 96.87 | 0.15 | 0.08 | 0.22 | 96.9 |
| 32.0 | 95.85 | 0.17 | 0.08 | 0.26 | 95.9 |
| 35.0 | 96.90 | 0.17 | 0.08 | 0.23 | 96.9 |
| 38.0 | 97.10 | 0.17 | N/D | 0.22 | 97.1 |
| 41.0 | 96.92 | 0.16 | 0.08 | 0.23 | 96.9 |
| 44.0 | 96.91 | 0.17 | 0.08 | 0.24 | 96.9 |
| 47.0 | 96.71 | 0.17 | 0.08 | 0.23 | 96.7 |

Conditions:
Temperature = 300° C.
Average LHSV = 1
Average 10% Oxygen in Nitrogen Feed Rate = 0.48 liters/hour

TABLE 2

Lifetime Study of the Dehydroisomerisation of Isobutenylcyclohexene Over a Palladium on Alumina Catalyst with Nitrogen Cofeed at 300° C.
This experiment shows that isobutylcyclohexane production increases with time on stream when a nitrogen cofeed is employed.

Liquid Products (% w/w)

| Time on Stream (hours) | isobutyl-benzene | isobutyl-cyclo-hexane | isobutyl-cyclo-hexene | iso-butenyl-benzene | Selectivity to isobutyl-benzene |
|---|---|---|---|---|---|
| 2.17 | 95.58 | 1.15 | 0.82 | 0.62 | 95.6 |
| 3.0 | 95.78 | 2.11 | 0.72 | N/D | 95.6 |
| 4.0 | 93.93 | 2.49 | 0.66 | 0.92 | 93.9 |
| 5.0 | 95.03 | 3.02 | 0.70 | 0.20 | 95.0 |
| 6.0 | 94.38 | 3.62 | 0.73 | 0.30 | 94.4 |
| 7.0 | 94.12 | 3.74 | 0.63 | 0.31 | 94.1 |
| 8.0 | 94.01 | 4.13 | 0.65 | 0.21 | 94.0 |
| 9.75 | 92.97 | 5.10 | 0.63 | 0.21 | 93.0 |
| 10.75 | 93.63 | 5.13 | 0.58 | 0.19 | 93.6 |
| 11.75 | 92.54 | 5.58 | 0.59 | 0.19 | 92.5 |
| 12.75 | 92.44 | 5.59 | 0.67 | 0.21 | 92.4 |
| 13.75 | 92.33 | 5.76 | 0.57 | 0.21 | 92.3 |
| 14.75 | 91.85 | 5.90 | 0.56 | 0.50 | 91.9 |
| 15.75 | 91.95 | 6.07 | 0.55 | 0.22 | 92.0 |
| 16.75 | 91.67 | 6.24 | 0.56 | 0.20 | 91.7 |
| 17.75 | 91.43 | 6.55 | 0.56 | 0.19 | 91.4 |
| 18.75 | 91.21 | 6.62 | 0.58 | 0.23 | 91.2 |
| 19.75 | 90.99 | 6.94 | 0.55 | 0.26 | 91.0 |

Conditions:
Temperature = 300° C.
Average LHSV = 1
Average Nitrogen Cofeed = 0.55 liters/hour

TABLE 3

Effect of Reaction Temperature on the Dehydroisomerisation of Isobutenylcyclohexene Over a Palladium Nitrate/Alumina Catalyst with 10% Oxygen in Nitrogen Cofeed
These experiments show the effect of reaction temperature on selectivity to isobutylbenzene, isobutylcyclohexane, isobutylcyclohexene and isobutenylbenzene.

| Reaction Temp (°C.) | 10% Oxygen in Nitrogen Cofeed (liters/hour) | Liquid Products (% w/w) | | | |
|---|---|---|---|---|---|
| | | isobutyl-benzene | isobutyl-cyclohexane | isobutyl-cyclohexene | isobutenyl-benzene |
| 250 | 0.49 | 94.77 | 2.44 | 0.09 | 0.04 |
| 275 | 0.49 | 96.21 | 0.99 | 0.129 | 0.08 |
| 300 | 0.50 | 96.32 | 0.36 | 0.177 | 0.24 |
| 325 | 0.57 | 94.50 | 0.37 | 1.36 | 1.07 |

Conditions:
Average LHSV = 1

TABLE 4

Lifetime Study of the Dehydroisomerisation of Isobutenylcyclohexene Over a Palladium Nitrate on Alumina Catalyst at a Liquid Hourly Space Velocity of 10 and a 10% Oxygen in Nitrogen Cofeed at 300° C.
This experiment shows the benefits to conversions and selectivities obtained using an oxygen/nitrogen cofeed.

Liquid Products (% w/w)

| Time on Stream (hours) | isobutyl-benzene | isobutyl-cyclo-hexane | isobutyl-cyclo-hexene | iso-butenyl-benzene | Selectivity to isobutyl-benzene |
|---|---|---|---|---|---|
| 1.08 | 95.55 | 1.63 | 0.12 | 0.16 | 95.6 |
| 4.08 | 96.62 | 0.51 | 0.24 | 0.19 | 96.6 |
| 7.08 | 96.46 | 0.34 | 0.33 | 0.25 | 96.5 |
| 10.08 | 96.51 | 0.28 | 0.31 | 0.30 | 96.5 |
| 13.08 | 96.85 | 0.24 | 0.17 | 0.33 | 96.9 |
| 16.08 | 96.65 | 0.14 | 0.25 | 0.32 | 96.7 |
| 19.08 | 96.64 | 0.23 | 0.23 | 0.32 | 96.6 |
| 22.08 | 96.66 | 0.18 | 0.22 | 0.41 | 96.7 |
| 25.08 | 96.31 | 0.11 | 0.30 | 0.64 | 96.3 |
| 28.08 | 96.18 | 0.26 | 0.48 | 0.58 | 96.2 |
| 31.08 | 96.53 | 0.24 | 0.34 | 0.39 | 96.5 |
| 34.08 | 96.53 | 0.24 | 0.30 | 0.37 | 96.5 |
| 37.08 | 96.48 | 0.22 | 0.24 | 0.38 | 96.5 |
| 40.08 | 96.71 | 0.21 | 0.24 | 0.39 | 96.7 |
| 43.08 | 96.38 | 0.23 | 0.21 | 0.39 | 96.4 |

TABLE 4-continued

Lifetime Study of the Dehydroisomerisation of
Isobutenylcyclohexene Over a Palladium Nitrate on Alumina
Catalyst at a Liquid Hourly Space Velocity of 10 and a 10%
Oxygen in Nitrogen Cofeed at 300° C.
This experiment shows the benefits to conversions and
selectivities obtained using an oxygen/nitrogen cofeed.

| Time on Stream (hours) | Liquid Products (% w/w) | | | | Selectivity to isobutyl- benzene |
|---|---|---|---|---|---|
| | isobutyl- benzene | isobutyl- cyclo- hexane | isobutyl- cyclo- hexene | iso- butenyl- benzene | |
| 46.08 | 96.61 | 0.22 | 0.19 | 0.36 | 96.6 |
| 49.08 | 96.65 | 0.21 | 0.20 | 0.36 | 96.6 |

Conditions:
Temperature (°C.) = 300
Average LHSV = 1
Average 10% Oxygen in Nitrogen Feed Rate = 0.45 liters/hour

TABLE 5

Lifetime Study of the Dehydroisomerisation of Isobutenylcyclohexene Over a Palladium on
Alumina Catalyst at an LHSV of 10 at 350° C.
This experiment shows rapid loss of conversion and selectivity to isobutylbenzene with time on stream
using an LHSV of 10.

| Time on Stream (hours) | Liquid Products (% w/w) | | | | Isobutenylcyclohexene Conversion | Selectivity to isobutyl- benzene |
|---|---|---|---|---|---|---|
| | isobutyl- benzene | isobutyl- cyclohexane | isobutyl- cyclohexene | isobutenyl- benzene | | |
| 1.0 | 93.89 | 3.40 | 0.10 | 0.40 | 100.0 | 93.9 |
| 4.0 | 90.20 | 5.24 | 1.66 | 0.44 | 99.9 | 90.3 |
| 7.0 | 68.62 | 1.46 | 12.22 | 11.36 | 97.4 | 70.5 |
| 10.0 | 38.90 | 0.69 | 21.02 | 19.79 | 87.0 | 44.7 |
| 13.0 | 24.93 | 0.50 | 25.51 | 21.23 | 76.7 | 32.5 |
| 16.0 | 16.21 | 0.37 | 27.52 | 20.19 | 68.0 | 23.8 |

Conditions:
Temperature (°C.) = 350
Average LHSV = 10

We claim:

1. A process for the production of an isobutylbenzene (IBB) from an isobutenylcyclohexene (IBCH) which process comprises contacting at elevated temperature an IBCH in the presence of a molecular oxygen-containing gas with a catalyst comprising a transition metal selected from the group consisting of cobalt, nickel, ruthenium, rhodium, palladium, iridium, platinum, and mixtures of two or more thereof, said transition metal being in a form selected from the elemental metal and a compound thereof, said transition metal being supported on alumina.

2. A process according to claim 1 wherein the IBCH is isobutenylcyclohexene.

3. A process according to claim 1 wherein the molecular oxygen-containing gas is either oxygen or oxygen diluted with one or more inert gases.

4. A process according to claim 1 wherein the molecular oxygen-containing gas is oxygen diluted with nitrogen.

5. A process according to claim 1 wherein the process is operated in the vapour phase.

6. A process according to claim 1 wherein the transition metal is palladium.

7. A process according to claim 1 wherein the transition metal comprises from 0.1 to 10% w/w of the catalyst, based on the weight of the support.

8. A process according to claim 1 wherein the IBCH is isobutenylcyclohexene and the process is operated in the vapour phase at a temperature in the range from 200° to 350° C.

9. A process according to claim 1 wherein the process is operated continuously.

* * * * *